(12) United States Patent
Sonnleitner

(10) Patent No.: US 10,247,699 B2
(45) Date of Patent: Apr. 2, 2019

(54) SYSTEM FOR DETECTING ELECTROPHORESIS

(75) Inventor: Max Sonnleitner, Linz (AT)

(73) Assignee: ASMAG-Holding GmbH, Gruenau im Almtal (AT)

( * ) Notice: Subject to any disclaimer, the term of this patent is extended or adjusted under 35 U.S.C. 154(b) by 702 days.

(21) Appl. No.: 12/312,759

(22) PCT Filed: Nov. 21, 2007

(86) PCT No.: PCT/EP2007/010066
§ 371 (c)(1),
(2), (4) Date: Nov. 23, 2009

(87) PCT Pub. No.: WO2008/061717
PCT Pub. Date: May 29, 2008

(65) Prior Publication Data
US 2010/0059379 A1    Mar. 11, 2010

(30) Foreign Application Priority Data
Nov. 23, 2006   (DE) .......................... 10 2006 055 876

(51) Int. Cl.
*C12Q 1/6874* (2018.01)
*G01N 27/447* (2006.01)
*C12Q 1/6869* (2018.01)

(52) U.S. Cl.
CPC ..... *G01N 27/44721* (2013.01); *C12Q 1/6874* (2013.01); *G01N 27/447* (2013.01); *G01N 27/44778* (2013.01); *C12Q 1/6869* (2013.01)

(58) Field of Classification Search
None
See application file for complete search history.

(56) References Cited

U.S. PATENT DOCUMENTS

| 3,432,414 A | 3/1969 | Rand |
| 5,629,533 A | 5/1997 | Ackley et al. |
| 6,027,624 A * | 2/2000 | Asouzu et al. ............ 204/452 |
| 6,184,990 B1 | 2/2001 | Amirkhanian et al. |
| 6,592,733 B1 | 7/2003 | Foley et al. |
| 2007/0292307 A1 | 12/2007 | Padinger et al. |

FOREIGN PATENT DOCUMENTS

| GB | 2369428 | 5/2002 |
| WO | 2006026796 A1 | 3/2006 |

OTHER PUBLICATIONS

International Search Report, PCT/EP2007/010066, dated Apr. 4, 2008.

* cited by examiner

*Primary Examiner* — Neil N Turk
(74) *Attorney, Agent, or Firm* — Collard & Roe, P.C.

(57) ABSTRACT

The invention describes a detection system (1) for analytical separation processes, particularly for electrophoresis, characterized by an optoelectronic sensor layer (5) made from organic semiconductor materials extending along the carrier layer (2) for the sample to be tested, for detecting the separated sample.

9 Claims, 3 Drawing Sheets

Figure 1:
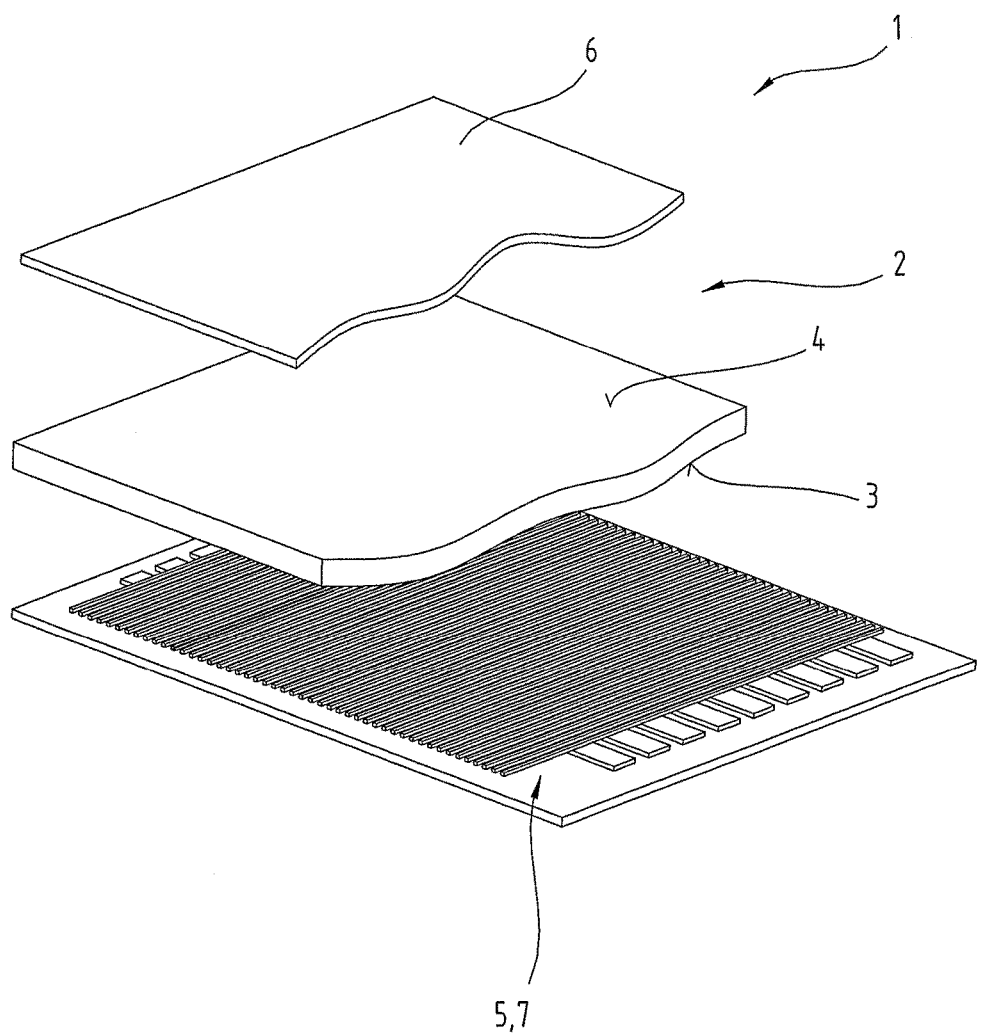

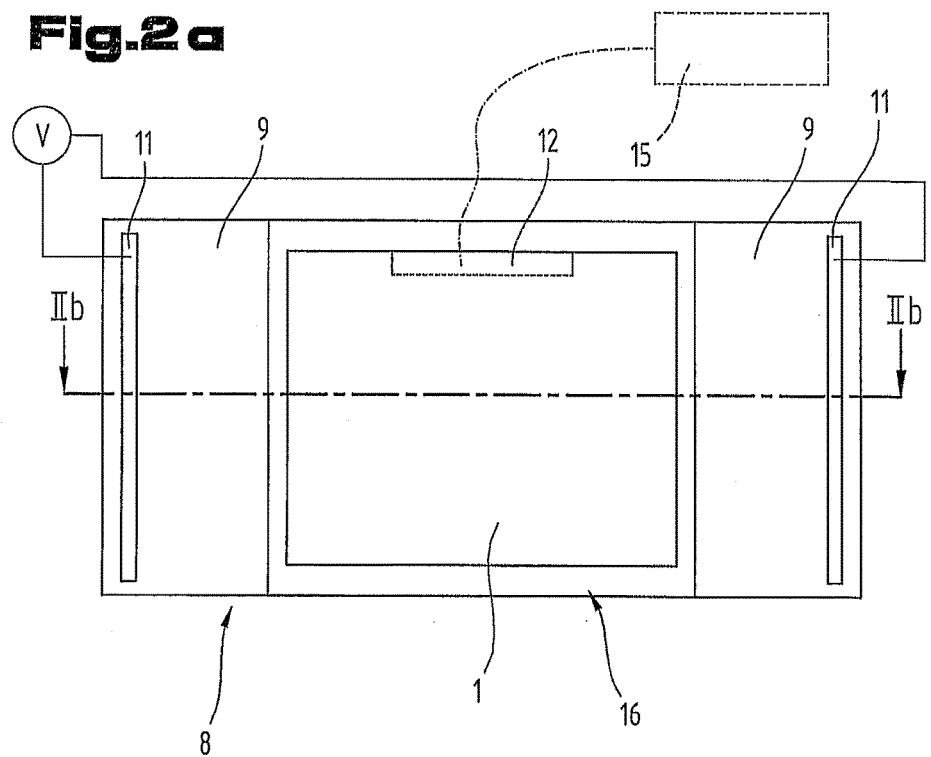
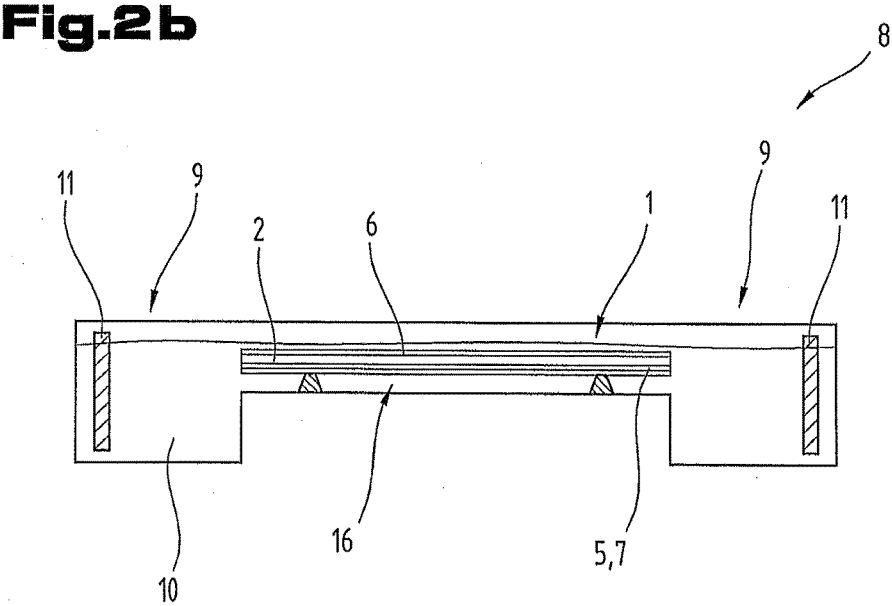

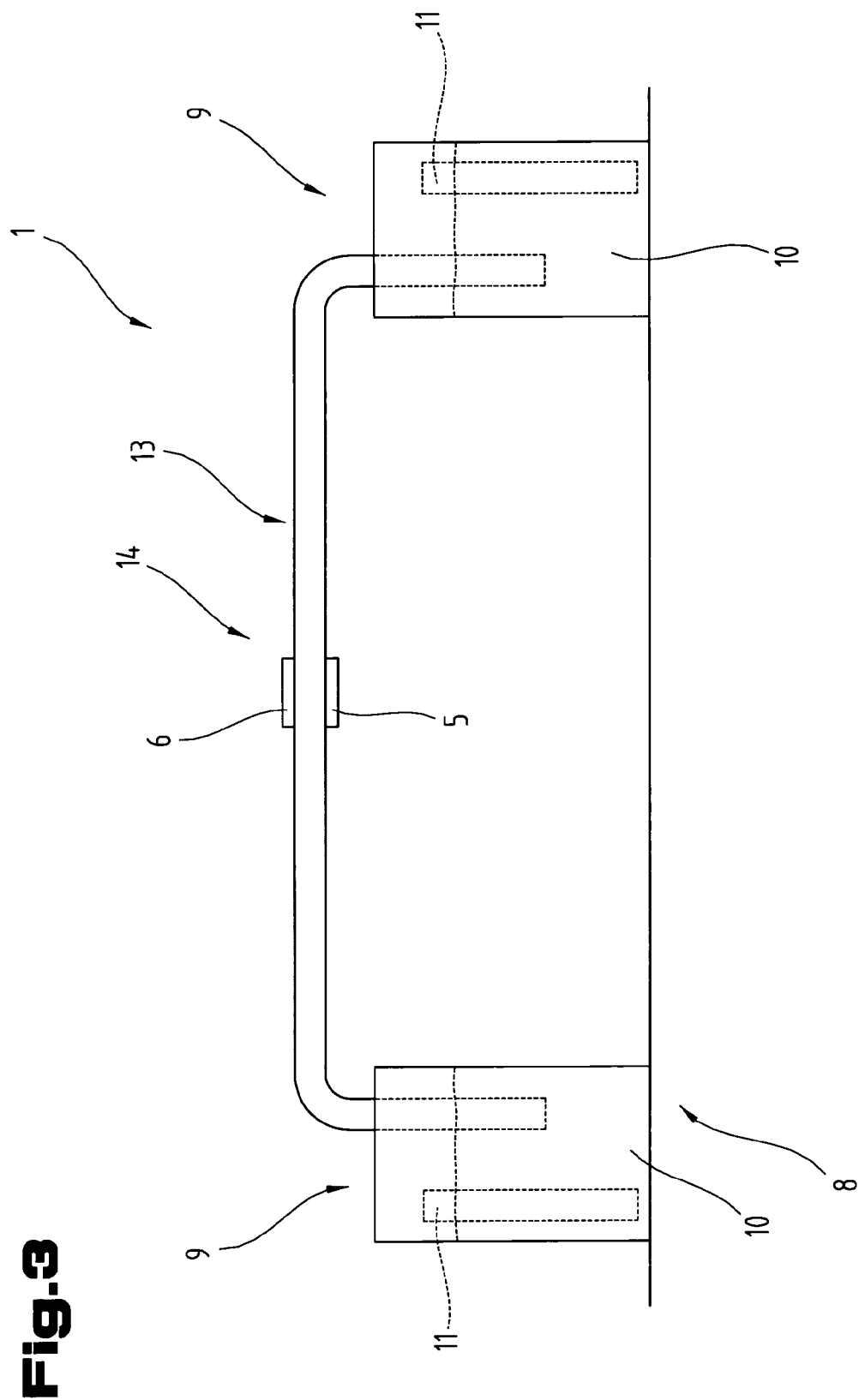

SYSTEM FOR DETECTING ELECTROPHORESIS

The invention relates to a system for detecting electrophoresis.

Electrophoresis belongs to the large group of analytical separation methods which differ from one another due to the force used to accomplish separation.

Alongside mechanical methods, which include separation methods based on gravity, centrifugal force or pressure, there are also thermal, chemical and magnetic or electrical methods, to which electrophoresis belongs.

All of these methods have in common the fact that the generated force causes or induces different velocities in the particles or molecules in a medium or carrier material in order to achieve spatial separation or migration. Electrophoresis can be used to detect the migration of electrically charged or polarized particles through a substance acting as a carrier material.

This migration is dependent on the particle size and the varied ion charge, in other words the individual substances or molecules each move through the carrier material at different speeds so that a separation takes place according to electrophoretic mobility. This can be detected with appropriate equipment.

CCD-camera based systems, for instance, are used for such purposes but they are, admittedly, relatively expensive.

Another option is the use of laser-based systems.

U.S. Pat. No. 6,184,990 B1 discloses an optical system, for instance, with a laser-based fluorescence detector which can be used for electrophoresis applications. One objective of the disclosed device in particular is to improve the collection efficiency and signal intensity of laser-induced fluorescence. In order to reflect the greatest possible portion of emitted light radiation into a lens array, the optical device includes a concave reflector.

U.S. Pat. No. 6,592,733 B1 also discloses a detector system for an electrophoresis device. It describes a device for inducing electrophoresis, in which a wave guide for optical electromagnetic radiation is positioned so that an external light source directs its emitted radiation into the wave guide and thus illuminates portions of the reaction areas. An optical detection means is placed above the device, which detection means preferably comprises a detector system, such as a CCD camera or a photodiode array.

A disadvantage of all of these systems is the limited surface area of the array or detection area, or a significant cost increase when increasing the size of the system. A further disadvantage is that electrophoresis is typically detected and analyzed separately from the device in which electrophoresis is induced. This separate arrangement requires numerous work steps and furthermore runs the risk that the results obtained could be impaired or distorted due to the fact that the sample has to be moved.

Accordingly, the underlying objective of the invention is to propose an arrangement which is not subject to any constraint in terms of its surface area, is cost-effective and simple in construction and application.

This objective is achieved by the invention in that electrophoretic mobility is detected by means of an optoelectronic sensor layer made from organic semiconductor material.

The fundamental advantage of this type of system resides in the fact that the sensor layer may be of any arbitrary dimensions. This applies not only to the size, in other words the length and width on a two-dimensional surface, but also the shape.

The carrier layer is therefore constructed to the same dimensions as the sensor layer.

This sensor layer, serving as an image collector, may be a photoactive layer made with an organic semiconductor material, which is placed between two electrode layers. This type of sensor layer is described in WO 2006/026796.

The detection system as a whole may comprise a layer which serves either to illuminate or excite, the carrier layer for the sample to be electrophoretically separated, and the sensor layer, and hence in principle is a three-layer system.

At this stage, reference should be made to the statements above regarding the common aspects of the various separation methods. From this it follows that, in principle, the device described by the invention with such a sensor layer may also be used with other analytical separation methods where it is necessary to detect and analyze mobility.

Particularly with electrophoresis as an analytical separation method, the transport medium is preferably an aqueous solution. This aqueous solution may be in gel form, for instance, which is poured into a device, such as a container, in order to achieve a suitable mechanical stability, and the first and second flat faces are therefore spaced apart from one another by the thickness of the gel. In order to introduce a sample material into the transport medium, the container is provided with at least one opening.

Quantum detectors, particularly those made from organic semiconductor material, have the particular advantage that their spectral sensitivity can be specifically adapted and optimized precisely to the electromagnetic radiation to be detected, for instance using so-called band gap engineering. Organic semiconductors have the further, especially unique advantage that their manufacture requires no energy-intensive processes, for instance no high-temperature or high vacuum processes are needed. An additional advantage is that the disposal of organic semiconductors has a much lower environmental impact than would be the case with inorganic semiconductors.

Semiconductor components which emit electromagnetic radiation in the optical wavelength and are designed to illuminate or excite the sample have the particular advantage that their emitted spectral range can be optimized specifically to the sample to be illuminated or transilluminated. A further advantage of semiconductor components resides in the fact that they can be constructed in an especially compact manner and require only a very small amount of energy at higher light density. A further advantage is that the emitted electromagnetic radiation is not generated by thermal processes.

As a light source, LEDs may be used, for instance, since these are widely available and thus cost-effective to employ. In a particularly advantageous embodiment, the light source may comprise LEDs made from an organic semiconducting material, known as so-called OLEDs. Organic semiconductor components have—as previously described—very unique advantages with respect to their manufacture, deployment and disposal. Due to their compact construction, semiconductor components have the further advantage that the generated electromagnetic radiation can predominantly be controlled in the direction of the sample material to be illuminated or excited, thereby largely eliminating undesired scattering effects.

In a particularly advantageous embodiment, the optoelectronic sensor layer is printed on the first flat face of the carrier layer. A printing process such as inkjet printing, screen printing or stamp printing has the particular advantage that the optoelectronic sensor layer can also be applied to the carrier layer retrospectively because the carrier layer and the optoelectronic sensor layer can be produced separately. An additional advantage is that printing processes do not require any energy intensive processes or work environments. Since printing processes are additive, structures can be produced that are not possible or are very difficult to produce with known, subtractive manufacturing processes used for semiconductor components.

In another advantageous embodiment, the optoelectronic sensor layer is constructed from organic semiconductor materials which are particularly well suited to manufacture using printing processes. Printed organic semiconductor components have the further advantage that, because of the extremely thin layers, very little material is needed. Since printing processes are additive, material waste through subsequent structuring, particularly the removal of previously applied material, is eliminated, offering a further cost advantage for printed organic semiconductor components.

In a further advantageous embodiment, the means for illuminating or exciting the sample are printed on the second flat face of the carrier layer. The advantages of printed layers, particularly for semiconductor components, have already been described. An especially advantageous embodiment is obtained if the claimed means are provided in the form of organic semiconductor components because such components are particularly well suited to manufacture with printing processes.

Because electrophoresis employs an optical effect, it is especially advantageous if the optoelectronic sensor layer and/or the medium for illuminating or exciting the sample is transparent or semi-transparent, because this permits unhindered visual control with the human eye in addition to detecting the reaction with detectors. Since the means for illuminating or exciting the sample are typically disposed uppermost, in other words facing the operator, it is of advantage if at least this layer is transparent or semi-transparent to electromagnetic radiation in the optically visible range. Likewise, the optoelectronic sensor layer may be transparent or semi-transparent so that an especially good and high-contrast visual evaluation of electrophoresis is possible.

In a further advantageous embodiment, the optoelectronic sensor layer extends at least partially along the carrier layer. With electrophoresis, an overall view of molecule movement, as well as a detailed image of a portion of the movement path of the molecules can be of interest. This advantageous embodiment ensures that the optoelectronic sensor layer may also be placed only over those portions of the carrier layer in which the anticipated molecule movement is to be detected.

Another type of analytic separation process is capillary electrophoresis, in which the carrier layer of the detection system proposed by the invention is disposed in a capillary. Capillary electrophoresis has the advantage that only very small amounts of sample fluid are required and a more rapid measurement is possible due to a higher velocity of molecule movement. With capillary electrophoresis, it is possible to detect the development of molecule movement as a function of time, rather than the complete picture of molecule movement.

An advantageous embodiment is obtained if the optoelectronic sensor layer and the medium for illuminating or exciting the sample are printed on opposite sides of the carrier layer. This construction ensures that the electromagnetic radiation emitted by the lighting means primarily acts on the optoelectronic sensor layer and thus also penetrates the sample material to be analyzed or detected.

The invention will be explained in more detail below with reference to examples of embodiments illustrated in the appended drawings.

The drawings are schematically simplified diagrams illustrating the following:

FIG. 1A simplified illustration of the detection system proposed by the invention;

FIG. 2 a) and b) A device for inducing electrophoresis, in which the detection system proposed by the invention is inserted;

FIG. 3 A different construction of the detection system proposed by the invention for carrying out capillary electrophoresis.

Firstly, it should be pointed out that the same parts described in the different embodiments are denoted by the same reference numbers and the same component names and the disclosures made throughout the description can be transposed in terms of meaning to same parts bearing the same reference numbers or same component names. Furthermore, the positions chosen for the purposes of the description, such as top, bottom, side, etc., relate to the drawing specifically being described and can be transposed in terms of meaning to a new position when another position is being described. Individual features or combinations of features from the different embodiments illustrated and described may be construed as independent inventive solutions or solutions proposed by the invention in their own right.

FIG. 1 shows the detection system 1 proposed by the invention, in which a carrier layer 2 comprises a first 3 and a second 4 flat face and in which an optoelectronic sensor layer 5 is disposed on the first flat face. If necessary, another lighting means 6 is placed over the second flat face 4.

The carrier layer 2 may be a container, for example, in which case an aqueous solution, particularly a gel-like substance, is placed inside and held in place by the walls of the container. The gel may be agarose, polyacrylamide, or also cellulose acetate, for example, such as used in known devices for carrying out electrophoresis. The carrying out of electrophoresis is considered to be generally understood, and so will not be described here in detail. Not illustrated in the drawings is the at least one opening in the container through which the sample material to be characterized can be introduced into the carrier layer.

The lighting means 6 for illuminating or exciting the sample may be provided in the form of a number of individual lighting means for example, particularly LEDs, and preferably organic LEDs (OLEDs) will be used. The advantage of these components is that they have a very compact construction, good energy efficiency and the spectral range of the emitted electromagnetic radiation can be accurately and reliably adjusted within a wide range. The lighting means may also be provided in the form of a single light element, for example, so that the entire covered sample area is illuminated or excited uniformly. A particular advantage of lighting means based on organic semiconductor components is that they can be placed on an existing carrier layer without energy intensive or complex manufacturing processes. Each lighting means can be individually activated, for instance by activating the supply electrodes with electric power in a grid pattern. Individual lighting elements can therefore be specifically activated and it is also possible in particular for the lighting elements to be excited to emit electromagnetic radiation with variable wavelengths.

The optical sensor layer 5 is provided in the form of a plurality of quantum detectors 7, which are preferably placed in a grid-like pattern. Quantum detectors, particularly semiconductor components such as phototransistors, photodiodes, or photoresistors, have the particular advantage that they have a very compact construction and thus offer a very high resolution based on a correspondingly dense arrangement. The set of quantum detectors making up the optoelectronic sensor layer may thus be constructed as an active or passive sensor matrix. The person skilled in the art will be familiar with the detailed construction of an active or passive sensor matrix and this aspect will therefore not be described in detail.

An important advantage of the detector system proposed by the invention resides in the fact that the optoelectronic sensor layer 5 is placed directly on the first flat face 3 of the carrier layer 2, and in particular, the individual quantum detectors are printed directly on the second flat face 4 of the carrier layer 2. This construction ensures that as small as possible a distance is maintained between the sample and the detection system, which in particular obviates the need for analysis or focusing optics. The small distance further ensures that even very weak reactions and low intensities in the sample can be easily and reliably detected. The small distance avoids the risk of scattering and cross-interactions, thereby preventing distorted measurements as far as possible. Since the optoelectronic sensor layer is printed directly onto the first flat face, it is preferably made from an electrically non-conducting material or an electrical isolation layer is provided on the first flat face.

Inducing electrophoresis renders the carrier layer 2 unusable and it must then be disposed of. According to advantageous embodiments, the optoelectronic sensor layer and the means for illuminating or exciting the sample may be made from organic semiconductor components. In view of the fact that the detection system 1 is used once only, the particular advantage of these embodiments is that the complete detection system can be disposed of in an environmentally friendly manner after a single use. Since organic semiconductors are particularly inexpensive to manufacture, especially by printing processes, and can even be applied to the carrier layer retrospectively, this type of detection system can be manufactured at low cost so that one-time use does not result in unreasonable costs and a completely new detection system is available for each electrophoresis.

The individual lighting means and quantum detectors are connected via interconnecting lines to a terminal area 12 and via it to an analysis device 15. The terminal area preferably comprises a coupling device affording fast and simple connection of the analysis device 15 to the detection system.

FIGS. 2 *a*) and *b*) show a device 8 for analytical separation processes, particularly for electrophoresis. One commonly known example of a device for carrying out electrophoresis comprises two chambers 9, filled with a solution 10, particularly a buffer solution. As can be seen from FIGS. 2*a*) and 2*b*), the two chambers are connected by a flow channel 16. The filling level is selected, so that the retained detection system 1 is in contact with or covered by the solution 10. After introducing a sample into the detection system 1 and applying an electrical voltage at the electrodes 11, a molecular movement is induced in the carrier layer of the detection system, whereby the speed of, and thus the distance traveled by, the individual molecules is dependent on the molecule size, for instance.

FIG. 2*b*) shows the lighting means 6 arranged adjacent to the carrier layer 2 and optoelectronic sensor layer 5, with all of these features arranged and immersed in the aqueous fluid.

In order to determine deflection and capture an image with known devices, the carrier layer must be removed from the solution and taken out of the device 8 and placed in an imaging system. Since electrophoresis is operated using aqueous solutions, this procedure poses a risk of contamination to the imaging device. There is an additional risk that the measurements will be distorted during transportation of the carrier layer, particularly due to shaking. Furthermore, due to the type of detection, an image can only be captured at specific times and a continuous capture and evaluation of the separation process is not possible with known processes.

The detection system proposed by the invention has the especially unique advantage that the electrophoresis can be detected continuously and in particular, it is not necessary to remove the detection system from the device 8. The detection system 1 proposed by the invention therefore permits continuous detection of molecule movement throughout the entire duration of the electrophoresis process. The detection system, particularly the quantum detectors and the lighting means, are constructed so that remaining in the solution 10 does not impair their respective functions and when used as intended, the lighting means and quantum detectors have no influence on the electrophoresis.

FIG. 3 shows a further construction of the detection system 1 proposed by the invention for carrying out capillary electrophoresis. The design of the device for analytic separation processes 8 is similar to the one already described in connection with FIG. 2 but the detection system proposed by the invention is not at least partially covered by the solution 10 in this instance.

In particular, the detection system 1 comprises a capillary 13, which connects the two chambers 9 to one another. Capillary electrophoresis, which is commonly known, does not capture the complete picture of molecule movement and instead, the detection device 14 plots a curve of the passing molecules as a function of time. Applying an electrical voltage across the electrodes 11 causes the molecules of the sample to be tested, which were introduced into the capillary 13, to move within the capillary. The velocity of the sample molecules is dependent on the size of the molecules, for example, which means that the migrating molecules pass by the detection device 14 at different instants.

The detection device comprises a lighting means 6 and an optoelectronic sensor layer 5, and, using an analysis device 15, the curve plotting the weakening of the elec-tromagnetic radiation penetrating the capillary can be determined as a function of time. In particular, the lighting means 6 emits electromagnetic radiation in the optical range, primarily in the direction of the optoelectronic sensor layer 5 which, because of the arrangement, means that the radiation also penetrates the capillary 13 and thus the carrier medium and sample material in the capillary. Due to the influence of the electromagnetic radiation on the molecules, a weakening of the radiation can occur, for instance, which can be detected with the optoelectronic sensor layer 5. Depending on the sample to be tested and the wavelength of the emitted electromagnetic radiation, however, excitation may also be detected.

The especially unique advantage of this detection systems resides in the fact that the detection device 14, in particular the lighting means 6 and the optoelectronic sensor layer 5 can be printed onto the capillary 13, whereby printing can take place as independently as possible from the production of the capillary. In particular, the detection device can be printed on a number of known capillaries which are designed for carrying out capillary electrophoresis. Integrating the detection device in the measuring device offers the particular advantage that the measuring device is simple to operate and, particularly in view of the fact that the detection device is inexpensive to manufacture, the detection system 1 proposed by the invention is especially well suited for one-time use.

All figures relating to ranges of values given in the substantive description should be construed as meaning that they include any and all part-ranges, e.g. the range 1 to 10 should be understood as meaning that it includes all part-ranges starting from the lower limit of 1 and up to the upper limit of 10, i.e. all part-ranges start with a bottom limit of 1 or higher and end with an upper limit of 10 or less, e.g. 1 to 1.7 or 3.2 to 8.1 or 5.5 to 10.

The embodiments illustrated as examples represent possible design variants of the detection system, and it should be pointed out at this stage that the invention is not specifically limited to the design variants specifically illustrated, and instead the individual design variants may be used in different combinations with one another and these possible variations lie within the reach of the person skilled in this technical field given the disclosed technical teaching. Accordingly, all conceivable design variants that can be obtained by combining individual details of the design variants described and illustrated are possible and fall within the scope of the invention.

LIST OF REFERENCE NUMBERS

1 Detection system
2 Carrier layer
3 First flat face
4 Second flat face
5 Optoelectronic sensor layer
6 Lighting means
7 Quantum detector
8 Device for analytical separation processes
9 Chamber
10 Solution
11 Electrode
12 Terminal area
13 Capillary
14 Detection device
15 Analysis Device
16 Flow channel

The invention claimed is:

1. A device for analytical separation processes, particularly for electrophoresis, comprising:
 a housing, the housing comprising two chambers connected by a flow channel, each of the two chambers having a respective chamber depth, the flow channel providing a fluid connection between the two chambers, wherein the flow channel has a flow channel depth which is less than the respective chamber depth of each of the two chambers;
 an electrode arranged in each chamber;
 an aqueous solution arranged within the two chambers and the flow channel;
 a sample to be analyzed disposed in the aqueous solution, wherein a voltage source is connected to the two electrodes, which voltage source applies a voltage to the electrodes resulting in electrophoretic separation of various particles within the sample and a movement of the sample to be analyzed along the flow channel;
 a detection device disposed in the flow channel, and immersed in the aqueous solution, wherein the two chambers and the flow channel are filled with the aqueous solution to a level such that the detection device is in contact with the aqueous solution, the detection device comprising:
 a carrier layer disposed in the flow channel, the carrier layer comprising a container filled with a substance for carrying out electrophoresis, wherein the container is configured such that the sample to be analyzed is introduced into the container;
 a light source comprising semiconductor components arranged adjacent to the carrier layer for illuminating the sample to be analyzed with electromagnetic radiation in a visible optical spectrum; and
 an optoelectronic sensor layer comprising a plurality of quantum detectors made from organic semiconductor materials, the optoelectronic sensor layer being printed onto a first flat face of the carrier layer and extending along the carrier layer, the quantum detectors being operable to detect a change of the electromagnetic radiation passing through the sample over time and to output an electrical signal corresponding to the change of the electromagnetic radiation.

2. The device according to claim 1, wherein the light source is disposed in layer form on top of the carrier layer.

3. The device as according to claim 1, wherein the optoelectronic sensor layer is coated with the organic semiconductor in a structured or homogenous manner.

4. The device according to claim 3, wherein the optoelectronic sensor layer comprises foil and also comprises strips disposed at a distance from one another, which are applied to the foil.

5. The device according to claim 1, wherein the carrier layer is constructed from laminar transport medium comprising a first and a second flat face.

6. The device according to claim 1, wherein the light source is further printed on a second flat face of the carrier layer.

7. The device according to claim 1, wherein the optoelectronic sensor layer and/or the light source are transparent or semi-transparent.

8. The device according to claim 2, wherein the optoelectronic sensor layer and the light source are printed opposite one another on the carrier layer.

9. The device according to claim 1, wherein the substance for carrying out electrophoresis is selected from the group consisting of agarose, polyacrylamide and cellulose acetate.

* * * * *